(12) United States Patent
Lundkvist

(10) Patent No.: US 9,404,901 B2
(45) Date of Patent: Aug. 2, 2016

(54) FLUID SAMPLE HOLDERS WITH PISTON VALVE

(75) Inventor: Mats Lundkvist, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 316 days.

(21) Appl. No.: 14/234,719

(22) PCT Filed: Jul. 25, 2012

(86) PCT No.: PCT/EP2012/064612
§ 371 (c)(1),
(2), (4) Date: Jan. 24, 2014

(87) PCT Pub. No.: WO2013/014195
PCT Pub. Date: Jan. 31, 2013

(65) Prior Publication Data
US 2014/0174212 A1 Jun. 26, 2014

(30) Foreign Application Priority Data
Jul. 28, 2011 (GB) .................................. 1113017.6

(51) Int. Cl.
| | |
|---|---|
| *G01N 30/16* | (2006.01) |
| *B01L 3/00* | (2006.01) |
| *B01L 3/02* | (2006.01) |
| *G01N 1/28* | (2006.01) |
| *G01N 30/04* | (2006.01) |
| *G01N 30/18* | (2006.01) |
| *G01N 30/20* | (2006.01) |

(52) U.S. Cl.
CPC .............. *G01N 30/16* (2013.01); *B01L 3/0217* (2013.01); *B01L 3/52* (2013.01); *B01L 3/565* (2013.01); *B01L 3/567* (2013.01); *G01N 1/28* (2013.01); *G01N 30/04* (2013.01); *B01L 2300/123* (2013.01); *B01L 2400/0478* (2013.01); *B01L 2400/0487* (2013.01); *B01L 2400/065* (2013.01); *G01N 30/18* (2013.01); *G01N 2030/204* (2013.01)

(58) Field of Classification Search
CPC ....... G01N 30/04; G01N 30/16; G01N 30/18; B01L 3/52; B01L 3/565; B01L 3/567
See application file for complete search history.

(56) References Cited

U.S. PATENT DOCUMENTS

| | | | | |
|---|---|---|---|---|
| 2,966,793 A | * | 1/1961 | Mullaney | ............... G01N 25/50 116/DIG. 18 |
| 4,202,769 A | | 5/1980 | Greenspan | |
| 5,097,747 A | * | 3/1992 | Levenez | ................. F16B 13/02 137/601.13 |
| 5,354,483 A | | 10/1994 | Furse | |
| 6,254,835 B1 | | 7/2001 | Feygin | |

FOREIGN PATENT DOCUMENTS

WO          93/22673          11/1993

OTHER PUBLICATIONS

PCT/EP2012/064612 ISRWO Dated Oct. 22, 2012.

* cited by examiner

*Primary Examiner* — Paul West
(74) *Attorney, Agent, or Firm* — Wood IP LLC

(57) ABSTRACT

Disclosed is a fluid sample holder 20 for delivering or receiving a fluid sample to or from fluid processing equipment such as a chromatography column 5 (FIG. 1). The sample holder 20 comprises a sliding seal 25 within a reservoir. The sliding seal 25 is displaceable within the reservoir 15 by means of a fluid pressure differential and includes a valve 260 operable when the sliding seal reaches or substantially reaches an end of its displacement, said valve including a stem 251 having a tapered portion 259 for cooperating with a tapering aperture 262 having a complementary taper, for substantially preventing fluid flow when so cooperating, said stem 251 being displaceable away from said aperture 262 and out of said cooperation at said end of its displacement, to open the valve 260.

20 Claims, 5 Drawing Sheets

FLUID SAMPLE HOLDERS WITH PISTON VALVE

This application is a filing under 35 U.S.C. 371 of international application number PCT/EP2012/064612, filed Jul. 25, 2012, which claims priority to Great Britain application number 1113017.6 filed Jul. 28, 2011, the entire disclosure of which is hereby incorporated by reference.

This invention relates to a sample holder, particularly, but not exclusively for allowing a fluid sample to be delivered to, or received from, a chromatography column or other fluid processing equipment.

Where small amounts of sample fluids need to be employed, for example in protein purification in a chromatographic process, in commercially available products, such sample fluids have been provided in fluid sample holders which have a reservoir connectable to a chromatography column. The reservoirs have an outlet for expelling the fluid and an inlet for accepting buffer fluid. In use the buffer fluid is pressurised to force the sample fluid out of the outlet. In order to separate the sample and buffer fluids, a moveable barrier between the sample fluid and the buffer fluid has been provided.

In the commercially available fluid sample holder this barrier is in the form of a sliding seal. It is known for the sliding seal to have a multi-part metal valve which opens when the seal reaches the end of its travel. This action allows the buffer fluid through the sliding seal to reach the sample fluid. This action allows buffer fluid to carry on pushing the sample fluid toward the chromatography column with minimal mixing and also allows the buffer fluid to attempt to clean the sample holder. However, the known valve is complicated, and consequently expensive. In addition, the large number of parts makes the valve difficult to clean.

An embodiment of the present invention addresses, the shortcomings mentioned above, as well as other problems with prior designs.

According to a first aspect of the invention, there is provided a fluid sample holder suitable for allowing a fluid sample to be delivered to, or received from, fluid processing equipment, the sample holder comprising: a sample fluid reservoir; a sample fluid port for providing fluid communication between said sample fluid reservoir and the fluid processing equipment; a buffer fluid port also for providing fluid communication between said reservoir and the fluid processing equipment; and a sliding seal within the reservoir including a sealing area which generally sealing engages with a wall of the reservoir thereby defining first and second fluid separated regions in the reservoir, the first region being in fluid communication with the sample fluid port, and the second region being in fluid communication with the buffer fluid port, the sliding seal being displaceable within the reservoir by means of a pressure differential between the first and second regions to thereby change the respective volumes of the first and second regions, and the sliding seal including a valve operable when the sliding seal reaches or substantially reaches an end of its displacement, said valve including a stem having a tapered portion for cooperating with a tapering aperture having a taper complementary to the tapered portion of the stem for substantially preventing fluid flow when so cooperating, said stem being displaceable away from said aperture and out of said cooperation at said end of its displacement, to open the valve.

In an embodiment, the sliding seal includes a body which includes said aperture, and said stem is resiliently mounted to the body so that said stem displacement with respect to the body is resilient and biased into said cooperation.

Preferably, the stem is resiliently mounted to the body by means of a resilient diaphragm.

In an embodiment, the body is formed from a one piece moulding, for example a one piece plastics moulding, and preferably, the stem and diaphragm are formed from another one piece moulding, preferably a one piece plastics moulding.

In an embodiment, the body includes a skirt extending away from the sealing area, said skirt having a distal end which includes an inwardly directed protrusion for holding the diaphragm.

Preferably, the skirt is castellated.

In an embodiment, the stem has an end portion which abuts an end element of the holder to cause the stem displacement relative to the body. In an embodiment, the sliding seal is cylindrical and has a centre axis, and the stem is displaceable parallel with the centre axis.

According to a second aspect of the invention there is provided a sliding seal for fluid separation of two regions of a fluid reservoir, the sliding seal being displaceable within the reservoir by means of a working fluid pressure differential between said two regions to thereby change the respective volumes of the two regions substantially without fluid flow past the seal, the seal comprising an external area for slidingly and sealingly engaging with a wall of the reservoir, the seal comprising a valve operable when the sliding seal reaches or substantially reaches an end of its displacement, said valve including a stem having a tapered portion for cooperating with a complementary tapered aperture for substantially preventing fluid flow when so cooperating, said stem being displaceable away from said aperture and out of said cooperation at said end of its displacement, to open the valve.

According to a third aspect of the invention there is provided fluid processing equipment, including a sample holder or a sliding seal as claimed in any one of the preceding claims.

According to a fourth aspect of the invention there is provided a chromatography column including a sample holder or a sliding seal as claimed in any one of the preceding claims.

According to a fifth aspect of the invention there is provided a method for delivering fluids to a chromatography column apparatus, including the steps of: providing a sample fluid holder containing a sample fluid; operating said apparatus to cause a buffer fluid to flow under a working pressure into said sample holder; causing a sliding seal within the sample holder to be displaced by said buffer fluid thereby causing only said sample fluid in the sample holder to exit the sample holder through a sample fluid port; allowing said displacement of said sliding seal to reach an end point thereat said working pressure is caused to increase; and causing the buffer fluid to flow through a valve in the sliding seal under the influence of said increased working pressure, when the sliding seal reaches or substantially reaches an end of its displacement, said valve including a stem having a tapered portion for cooperating with a complementary tapered aperture for substantially preventing fluid flow when so cooperating, said stem being displaceable away from said aperture and out of said cooperation at said end of its displacement, to open the valve.

Preferably, the method employs a sample holder having any one of the features according to the first aspect.

The invention extends to any feature described herein for example, a sample holder, fluid processing equipment, or chromatography column substantially as described herein, optionally with reference to the drawings.

The invention can be put into effect in numerous ways, one embodiment only being described below, with reference to the accompanying drawings, wherein.

Figure 1:
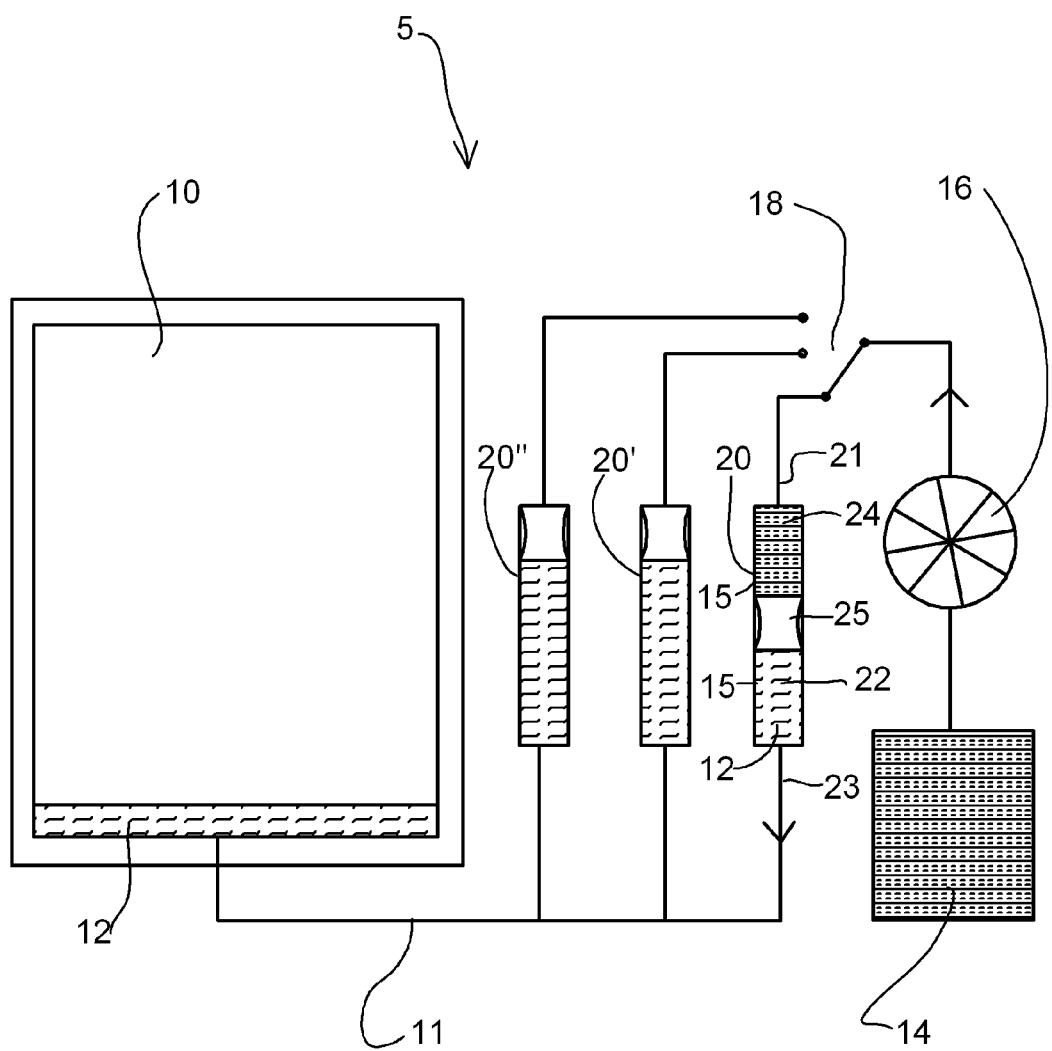
FIG. 1 shows a general arrangement of a sample holder in use with fluid processing equipment.

Referring to FIG. 1 there is shown schematically fluid processing equipment 5 in the form of a chromatographic column 10, having a supply conduit 12, fed, in this case, by three fluid sample holders 20, 20' and 20". Each sample holder is the same but sample holder 20 is described in more detail below. The sample holder 20 has an internal first region 22 and second region 24. The first region 22 retains a sample fluid, whereas a second region 24 receives a buffer fluid 14. The sample holder 20 is selectively connected to a pump 16, via a selection valve 18, and is able to receive buffer fluid under pressure via a buffer fluid port 21. The sample holder 20 has a sliding seal 25 which moves under the influence of the pressurised buffer fluid 14 and causes the sample fluid in the first region 22 to flow out of the holder 20 through a sample fluid port 23. The sample fluid flows into the chromatography column 10 where it is employed. For example, the sample could be used in a process for the purification of proteins.

To this point the described features are conventional. However, the construction of the sample holder 20 has been improved, and these improvements are described below.

Figure 2:
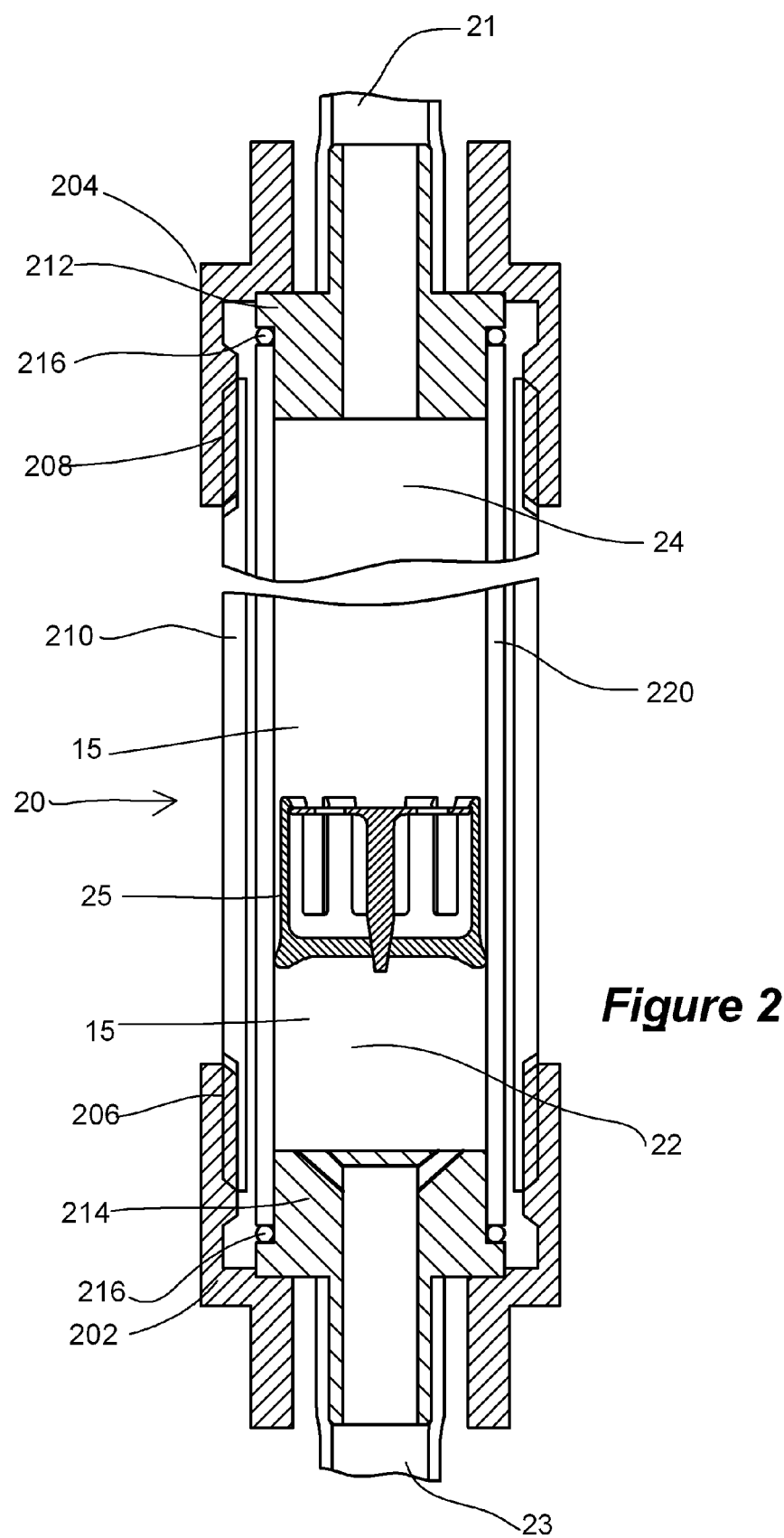
FIG. 2 shows a section through a sample holder of the type shown generally in FIG. 1.

With additional reference to FIG. 2, the holder 20 has two end fittings 202 and 204 which each include an integral threaded portion 206 and 208 respectively. The threaded portions each fit with an outer tube 210 having complementary threaded ends. The two end fittings are rotated to clamp a pipe connector 212 and 214 to each end of an inner tube 220. A sealing ring 216 between each pipe connector and the inner tube 220 provides a fluid tight seal. The ports 23 and 21 are formed by apertures in the pipe connectors 214 and 212. Thus, a sealed holder 20 is provided which has two ports for fluid communication with fluid processing equipment described above. Both the inner and outer tubes may be formed from transparent material, and it is preferred that the inner tube 220 is formed from glass material to provide a relatively inert sample wall surface and the outer tube is formed from a transparent or translucent plastics material to catch any shattered glass should the inner tube break under pressure.

Figure 3:
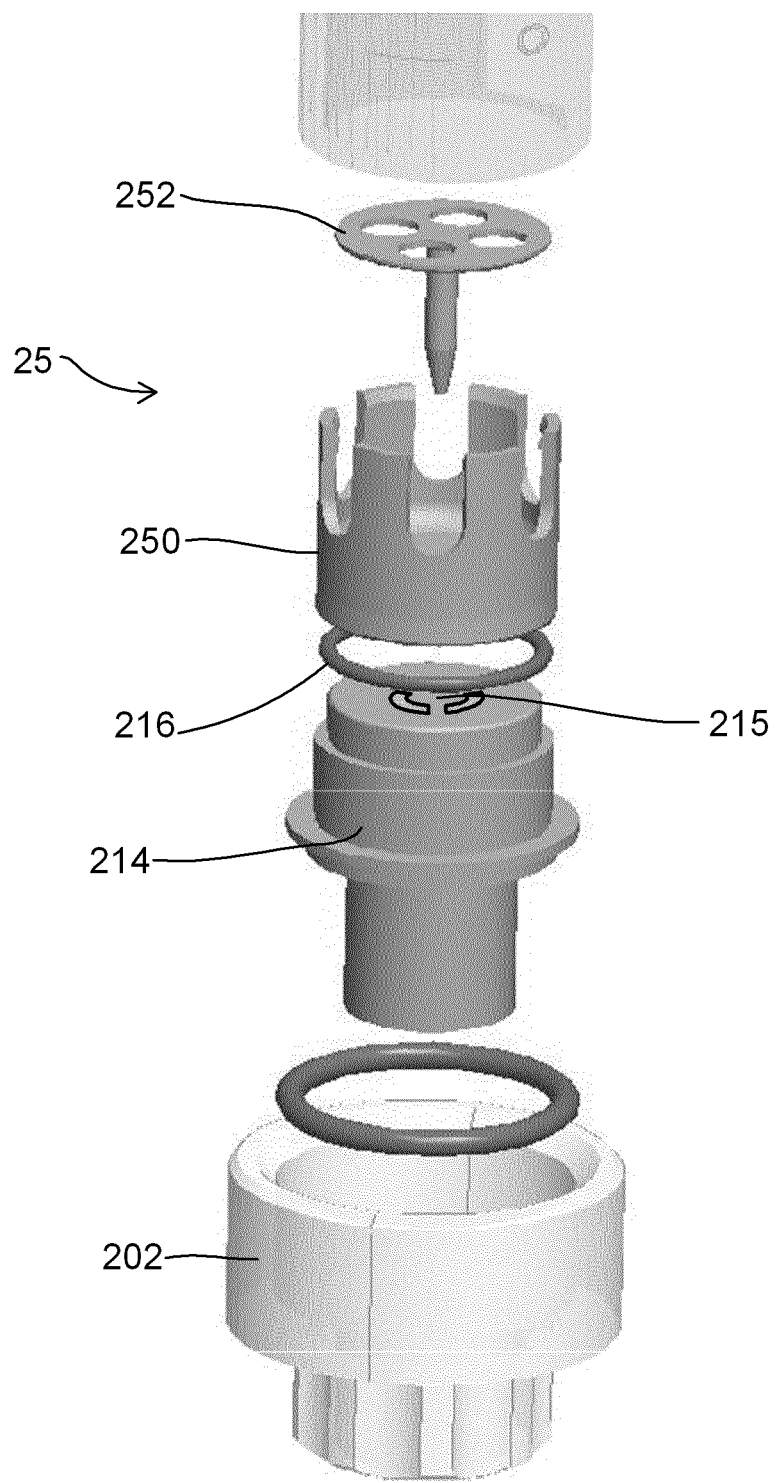
FIG. 3 shows an exploded pictorial view of some of the parts shown in FIG. 2.

FIG. 3 shows an exploded view of the lower end components of the sample holder shown in FIG. 2. It can be seen that the sliding seal 25 has two pieces: a main body 250; and a stem piece 252, both described in more detail below. The main body 250 and a stem piece 252 are each formed from moulded material, for example a one piece moulded plastics, such as a polyetheretherketone (PEEK), a polypropylene (PP) or a high density polypropylene (HDPP). The pipe connector 214 has an abutment element 215 which abuts with the stem piece 252 when the sliding seal 25 is positioned adjacent the connector 214, that is, when the seal is at or approaching its limit of travel.

Figure 4:
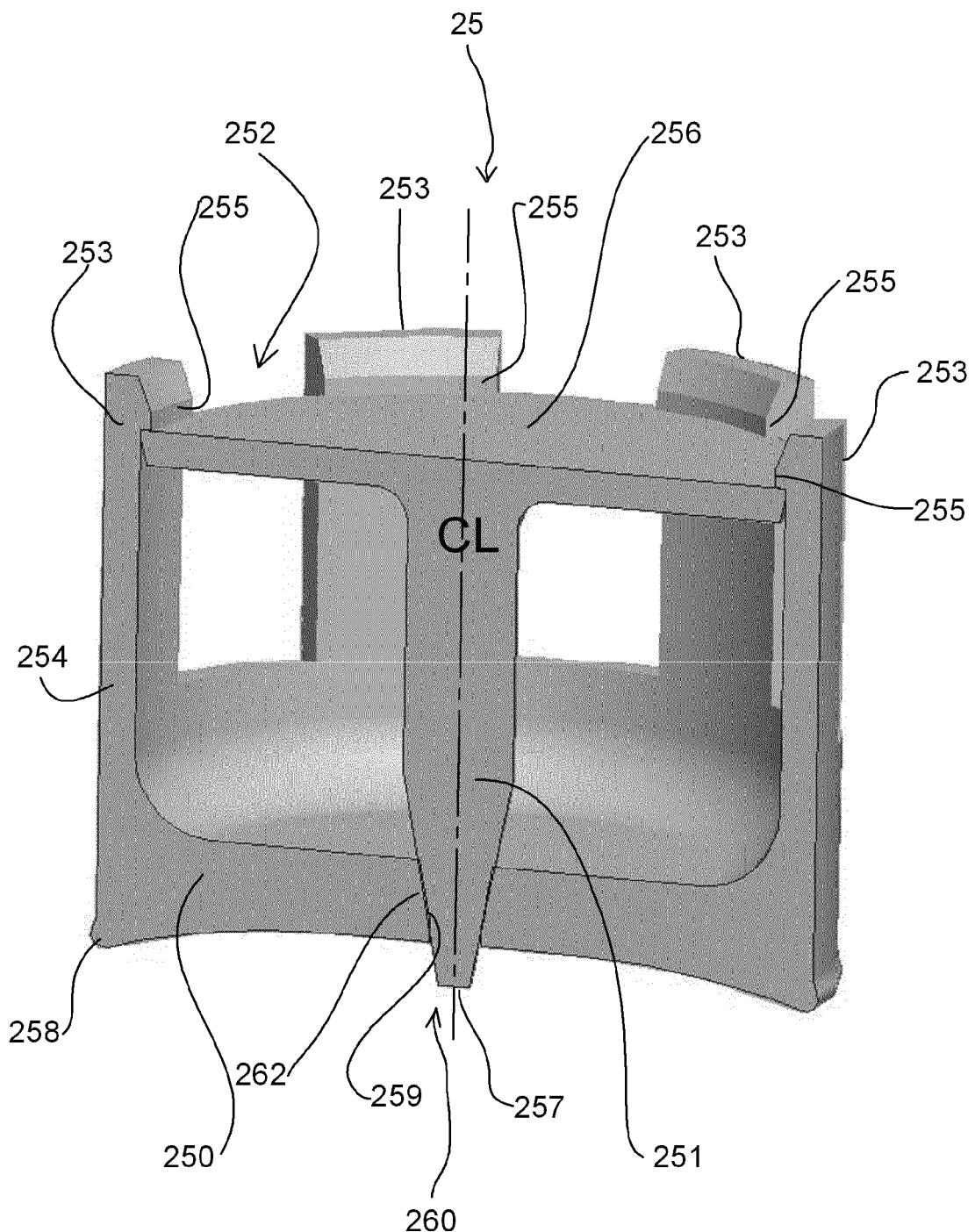
FIG. 4 shows a sectional pictorial view of a sliding seal of the type shown in FIG. 3.

FIG. 4 shows an enlarged sectional view of the sliding seal 25. The seal is generally cylindrical with a centre axis CL along which the seal 25 will travel in use. The seal has an external sealing area in the form of a lip 258 which resiliently abuts an inner face of the inner tube 220 to provide a sliding fluid seal. The seal 25 further includes a skirt 254 which is castellated to form a plurality of arms 253 spaced around the circumference of the body 250. Each arm 253 has a protrusion 255 extending towards the centre line CL.

The stem portion 252 has a stem 251 and a diaphragm 256. The diaphragm is relatively thin in section and will deflect when an abutment portion 257 at the end of the stem 251 is forced against the abutment element 215 as mentioned above. The protrusions 255 prevent the diaphragm from moving upwardly relative to the main body 250, and so the stem will return resiliently to its starting position when it is not under load.

The stem 251 includes also a tapered portion 259 which fits in fluid sealing manner in the complementary tapered of an aperture 262 in the main body 250. Thus the stem and aperture cooperate to act as a valve, given the reference 260 in FIG. 4, substantially preventing fluid flow other than when the stem is dislodged from the aperture by the abutment of the stem with the connector abutment element 215 as mentioned above.

Figure 5:
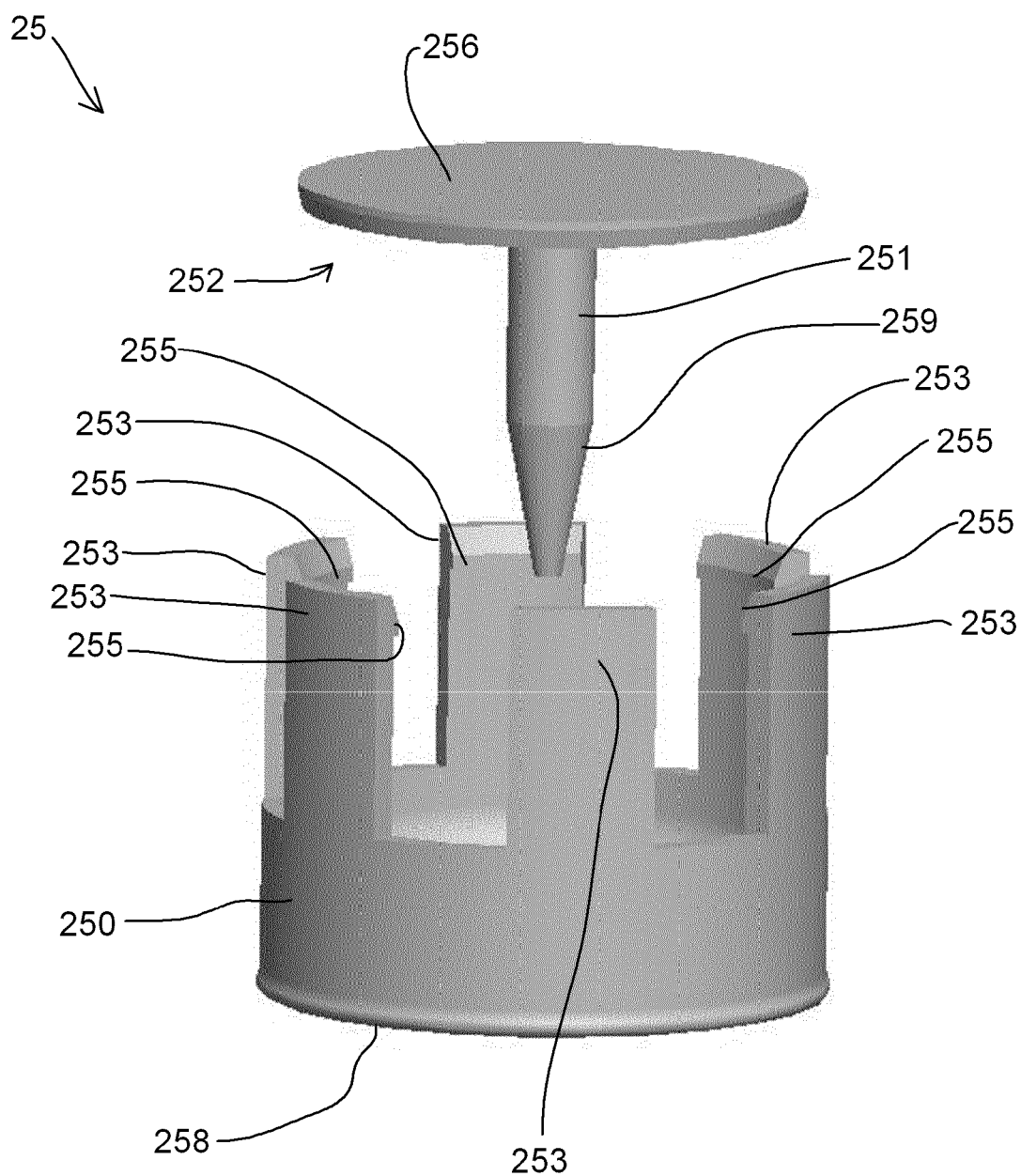
FIG. 5 shows a pictorial exploded view of a sliding seal shown in FIG. 4.

FIG. 5 is a further exploded view showing the sliding seal 25.

In FIG. 3 the diaphragm of the stem piece 252 has a series of apertures, whereas the diaphragm 256 shown in FIGS. 4 and 5 has none. In practice, the resilience of the diaphragm can be altered by its configuration and apertures or other changes to the configuration of the diaphragm are possible to change the characteristics of the valve 260.

Tests were conducted using the sliding seal shown in FIG. 3, and the results showed that under varying temperatures the maximum back pressure, that is the pressure differential in the sample and buffer regions when the sliding seal approached the point at which it opens, did not exceed 0.08 MPa. So the valve 260 will open at a relatively low pressure when the sliding seal is in the correct position.

It will be apparent to the skilled addressee that additions, omissions or modifications to the foregoing description are possible within the ambit of the invention defined herein.

For example, the use of the terms up or upper etc. and down, lower or lowermost etc. are used to describe the arrangement illustrated, and are not intended to limit possible alternative orientations. The term 'fluid' is used to include liquids and other fluent material, including but not limited to gases and fluent particulate or gel-like materials. The invention is primarily intended to introduce fluids in to the equipment described above, but could also be used to collect samples from fluid processing equipment by reversing the pressure differential. The holder described lends itself to automated equipment where the sample holder needs to be completely emptied and either flow needs to continue to push sample fluid into the equipment or the holder needs to flushed with buffer fluid, for example, prior to being disconnected from the equipment. However, the continuation of flow, or the flushing steps need not be employed.

The invention claimed is:

1. A fluid sample holder suitable for allowing a fluid sample to be delivered to, or received from, a fluid processing equipment, the sample holder comprising: a sample fluid reservoir; a sample fluid port for providing fluid communication between said sample fluid reservoir and said fluid processing equipment; a buffer fluid port also for providing fluid communication between the reservoir and the fluid processing equipment; and a sliding seal within the reservoir including a sealing area which generally sealingly engages with a wall of the reservoir thereby defining a first and a second fluid separated region in the reservoir, said first region being in fluid communication with the sample fluid port, and said second region being in fluid communication with the buffer fluid port, said sliding seal being displaceable within the reservoir by means of a pressure differential between said first and second regions to thereby change the respective volumes of the first and second regions, and the sliding seal including a valve operable when the sliding seal reaches or substantially reaches an end of its displacement, said valve including a stem having a tapered portion for cooperating with a complementary tapered aperture for substantially preventing fluid flow when so cooperating, said stem being displaceably away from said aperture and out of said cooperation at said end of its displacement, to open the valve, wherein the sliding seal includes a body which includes the aperture, and the stem is resiliently mounted to the body so that the stem's displacement with respect to the body is resilient and biased into said cooperation.

2. A fluid sample holder as claimed in claim 1, wherein the stem is resiliently mounted to the body by means of a resilient diaphragm.

3. A fluid sample holder as claimed in claim 2, wherein the body is formed from a one piece moulding and the stem and diaphragm are formed from another one piece moulding.

4. A fluid sample holder as claimed in claim 1, wherein the body includes a skirt extending away from the sealing area, said skirt having a distal end which includes an inwardly directed protrusion for holding the diaphragm.

5. A fluid sample holder as claimed in claim 4, wherein the skirt is castellated.

6. A fluid sample holder as claimed in claim 1, wherein the stem has an end portion which abuts an end element of the holder to cause said stem displacement relative to the body.

7. A fluid sample holder as claimed in claim 1, wherein the sliding seal is cylindrical and has a centre axis, and the stem is displaceably parallel with the centre axis.

8. A fluid processing equipment, including a sample holder as claimed in claim 1.

9. A chromatography column including a sample holder as claimed in claim 1.

10. A sliding seal for fluid separation of two regions of a fluid reservoir, the sliding seal being displaceable within the reservoir by means of a working fluid pressure differential between said two regions to thereby change the respective volumes of the two regions substantially without fluid flow past the seal, the seal comprising an external area for slidingly and sealingly engaging with a wall of the reservoir, the seal comprising a valve operable when the sliding seal reaches or substantially reaches an end of its displacement, said valve including a stem having a tapered portion for cooperating with a complementary tapered aperture for substantially preventing fluid flow when so cooperating, said stem being displaceably away from said aperture and out of said cooperation at said end of its displacement, to open the valve, wherein the sliding seal includes a body which includes the aperture, and the stem is resiliently mounted to the body so that the stem's displacement with respect to the body is resilient and biased into said cooperation.

11. A sliding seal as claimed in claim 10, wherein the stem is resiliently mounted to the body by means of a resilient diaphragm.

12. A sliding seal as claimed in claim 11, wherein the body is formed from a one piece moulding and the stem and diaphragm are formed from another one piece moulding.

13. A sliding seal as claimed in claim 10, wherein the body includes a skirt extending away from the sealing area, said skirt having a distal end which includes an inwardly directed protrusion for holding the diaphragm.

14. A sliding seal as claimed in claim 13, wherein the skirt is castellated.

15. A sliding seal as claimed in claim 10, wherein the sliding seal is part of a fluid sample holder and the stem has an end portion which abuts an end element of the holder to cause said stem displacement relative to the body.

16. A sliding seal as claimed in claim 10, wherein the sliding seal is cylindrical and has a centre axis, and the stem is displaceably parallel with the centre axis.

17. A fluid processing equipment, including a sliding seal as claimed in claim 10.

18. A chromatography column including a sliding seal as claimed in claim 10.

19. A method for delivering fluids to a chromatography column apparatus, including the steps of:
providing a sample fluid holder containing a sample fluid;
operating said apparatus to cause a buffer fluid to flow under a working pressure into said sample holder;
causing a sliding seal within the sample holder to be displaced by said buffer fluid thereby causing only said sample fluid in the sample holder to exit the sample holder through a sample fluid port;
allowing said displacement of said sliding seal to reach an end point thereat said working pressure is caused to increase; and
causing the buffer fluid to flow through a valve in the sliding seal under the influence of said increased working pressure, when the sliding seal reaches or substantially reaches an end of its displacement, said valve including a stem having a tapered portion for cooperating with a complementary tapered aperture for substantially preventing fluid flow when so cooperating, said stem being displaceably away from said aperture and out of said cooperation at said end of its displacement, to open the valve.

20. A method as claimed in claim 19, wherein the sample holder is suitable for allowing a fluid sample to be delivered to, or received from, the chromatography column apparatus, the sample holder comprising: a sample fluid reservoir; a sample fluid port for providing fluid communication between said sample fluid reservoir and the chromatography column apparatus; a buffer fluid port also for providing fluid communication between the reservoir and the chromatography column apparatus; and a sliding seal within the reservoir including a sealing area which generally sealingly engages with a wall of the reservoir thereby defining a first and a second fluid separated region in the reservoir, said first region being in fluid communication with the sample fluid port, and said second region being in fluid communication with the buffer fluid port, said sliding seal being displaceable within the reservoir by means of a pressure differential between said first and second regions to thereby change the respective volumes of the first and second regions, and the sliding seal including a valve operable when the sliding seal reaches or substantially reaches an end of its displacement, said valve including a stem having a tapered portion for cooperating with a complementary tapered aperture for substantially preventing fluid flow when so cooperating, said stem being displaceably away from said aperture and out of said cooperation at said end of its displacement, to open the valve.

* * * * *